US012721670B2

(12) United States Patent
Kleyman

(10) Patent No.: US 12,721,670 B2
(45) Date of Patent: Sep. 1, 2026

(54) LAPAROSCOPIC AND OPEN SURGERY END EFFECTOR JAW STRUCTURE AND METHOD

(71) Applicant: Gennady I Kleyman, Brooklyn, NY (US)

(72) Inventor: Gennady I Kleyman, Brooklyn, NY (US)

(73) Assignee: Expandoheat, L.L.C., Atlantic Heights, NJ (US)

( * ) Notice: Subject to any disclaimer, the term of this patent is extended or adjusted under 35 U.S.C. 154(b) by 0 days.

(21) Appl. No.: 19/337,641

(22) Filed: Sep. 23, 2025

(65) Prior Publication Data

US 2026/0069347 A1 Mar. 12, 2026

Related U.S. Application Data

(62) Division of application No. 18/116,900, filed on Mar. 3, 2023, now Pat. No. 12,446,951.

(51) Int. Cl.
*A61B 18/14* (2006.01)
*A61B 18/18* (2006.01)
(Continued)

(52) U.S. Cl.
CPC ...... *A61B 18/1445* (2013.01); *A61B 18/1815* (2013.01); *A61B 2018/00083* (2013.01);
(Continued)

(58) Field of Classification Search
CPC . A61B 18/1815; A61B 18/1445; A61B 18/04; A61B 18/085; A61B 18/10; A61B 18/1442; A61B 18/18; A61B 2018/00791; A61B 2018/00958; A61B 2018/128; A61B 2018/00083; A61B 2018/1823; A61B 2018/00601; A61B 2018/087; A61B 2018/1273; A61B 2018/1853; A61B 2018/1869; A61B 2018/1452; A61B 2018/1455; A61B 2018/167;
(Continued)

(56) References Cited

U.S. PATENT DOCUMENTS 8,343,144 B2 * 1/2013 Kleyman ........... A61B 18/1815 606/33
9,333,034 B2 5/2016 Hancock
(Continued)

*Primary Examiner* — Thomas A Giuliani

(57) ABSTRACT

Disclosed is a working end of a surgical instrument for delivering heat energy to tissue and (RF) energy for cutting tissue of different modalities. The working end includes paired first and second metal jaw members movable between open and closed positions, with each jaw member defining a jaw body and jaw end-effecter for engaging and heating tissue for the sealing of the tissue or vessels, or welding and coagulation of the tissue and jaw structure capable of generating radiofrequency (RF) energy for cutting tissue. Jaw members contain a microwave emitter coupled to a microwave energy source, the emitter is located within the jaw end effecter, which effecter includes an insert made of a microwave energy absorbing material which converts microwave energy into the heat energy. Jaw members also contain electrodes located within the jaw effecter end coupled to a radiofrequency (RF) energy source for procedures including tissue cutting, etc.

7 Claims, 7 Drawing Sheets

(51) Int. Cl.
*A61B 18/00* (2006.01)
*A61B 18/12* (2006.01)

(52) U.S. Cl.
CPC ............... *A61B 2018/00601* (2013.01); *A61B 2018/00791* (2013.01); *A61B 2018/126* (2013.01); *A61B 2018/1823* (2013.01)

(58) Field of Classification Search
CPC .... A61B 2018/126; A61B 2018/00404; A61B 2018/00607; A61B 2018/00619; A61B 2018/0063; A61B 2018/00994; A61B 2018/00428; A61B 2018/00589; A61B 2018/00595
USPC ......... 606/27–30, 33, 34, 37, 38, 41, 42, 48, 606/50–52; 607/96, 98, 99, 101, 102, 607/113, 115, 116, 156
See application file for complete search history.

(56) References Cited

U.S. PATENT DOCUMENTS

2009/0062786 A1* 3/2009 Garito .................... A61B 18/12 606/37
2020/0315691 A1* 10/2020 Minnelli ............ A61B 18/1445
2022/0168040 A1* 6/2022 Akagane ............ A61B 18/1445

* cited by examiner 20
24
48
25
44
27
12
54
53
RF bipolar
22
52
46
11
8
microwave 24
44
25
42
22
11
8
46

22
11
24
46
25
44

62
22
54
53
52

LAPAROSCOPIC AND OPEN SURGERY END EFFECTOR JAW STRUCTURE AND METHOD

Priority is claimed on Non-Provisional U.S. Pat. No. 12,446,951, application Ser. No. 18/116,900 filed 3 Mar. 2023, entitled LAPAROSCOPIC AND OPEN SURGERY END EFFECTOR JAW STRUCTURE AND METHOD and Provisional Patent Application No. 63/410,346 filed 27 Sep. 2022, entitled LAPAROSCOPIC AND OPEN SURGERY END EFFECTOR JAW STRUCTURE AND METHOD.

FIELD OF THE INVENTION

The invention relates to electrosurgical apparatus like metal jaw structure and method for sealing of blood vessels and tissue, for tissue fusion, welding and coagulation of tissue and for tissue cutting by utilizing electromagnetic energy.

BACKGROUND TO THE INVENTION

Conventional open and laparoscopic procedures typically involve sealing of vessels and tissues, as well as for welding and coagulation of tissues and tissue cutting or dissecting.

U.S. Pat. No. 8,343,144 provides a jaw structure configured with an antenna or applicator, for the delivery of electromagnetic energy in microwave range to a jaw structure, in which the portion of the jaw structure that is made out of the material impregnated with particles or fillers that absorb electromagnetic energy. During the process of absorption of the microwave energy, microwave absorbing material is transferred microwave energy into the heat. The generated heat is applied to the treated tissue by means of capturing the tissue in the jaw structure and applying pressure on the tissue, thus causing, depending on the used medical procedure, the sealing of the tissue or vessels, or welding and coagulation of the tissue.

With advantages of the devices by this patent, in surgical procedures for vessels sealing, or welding and coagulation of the tissue, those devices cannot provide tissue cutting or dissecting.

U.S. Pat. No. 9,333,034 the invention relates to electrosurgical apparatus in which radiofrequency and microwave frequency energy is used to treat biological tissue. In particular, this patent provides a surgical apparatus capable of generating radiofrequency (RF) energy for cutting tissue and microwave frequency energy for hemostasis (i.e. sealing broken blood vessels by promoting blood coagulation).

Disadvantage of this patent is a difficulty to control an area of microwave energy distribution and that can cause an unwanted thermal damage to tissue not intended to be heated or have any thermal damage.

SUMMARY OF THE INVENTION

The present invention addresses at least the above-described problems and/or disadvantages and provides at least the advantages described below.

Accordingly, an aspect of the present invention end effector comprises facing jaws, wherein a jaw with a metal body is configured for heating and cutting biological tissue. The jaw structure configured with an antenna, for the delivery of electromagnetic energy in microwave range to a microwave absorbing material portion, which is typically material impregnated with particles or fillers that absorb electromagnetic energy. During the process of absorption of the microwave energy in the microwave absorbing material portion from the microwave energy emitted by the antenna, the microwave energy is transferred into heat. In use, tissue or vessels to be treated are captured between the facing jaws, and with the jaws, pressure is applied on the tissue depending on the medical procedure used, The microwave generated heat is then applied to the captured tissue for procedures such as sealing of the tissue or vessels, or welding and coagulation of the tissue. Microwave frequencies range between $10^9$ Hz (1 GHz) to 1000 GHz. In addition to the microwave antenna in the jaw structure providing heat, the jaw is also configured with RF electrodes which are connected to a separate source of radio-frequency (RF) current in the range of from 100 kHz to 40 MHz to perform a bipolar cutting of the tissue located between the jaws and cutting frequency. The RF electrodes are electrically insulated from the microwave absorbing material and the metal jaws body.

An another embodiment, one of the jaws of end effector further includes an RF monopolar electrode for tissue cutting, and is also connected to a second source of RF energy having a frequency in the range of from 100 kHz to 40 MHz, which may be independent from RF energy supplied to jaw bipolar electrodes and cutting. The monopolar electrode can be located in the distal portion one of the jaws and this electrode electrically is insulated from jaw body except where contact is desired, and from the microwave absorbing material and bipolar RF electrodes. The patient return electrode (also known as a ‘dispersive pad’) is placed somewhere else on the patient's body (not shown). Upon application of a desired amount of RF energy, the tissue in contact with monopolar electrode will be cut or dissected.

BRIEF DESCRIPTION OF THE DRAWING

The above and other aspects, features and advantages of the present invention will become more apparent from the following detailed description when taken in conjunction with the accompanying drawing in which.

DETAILED DESCRIPTION

Figure 1:
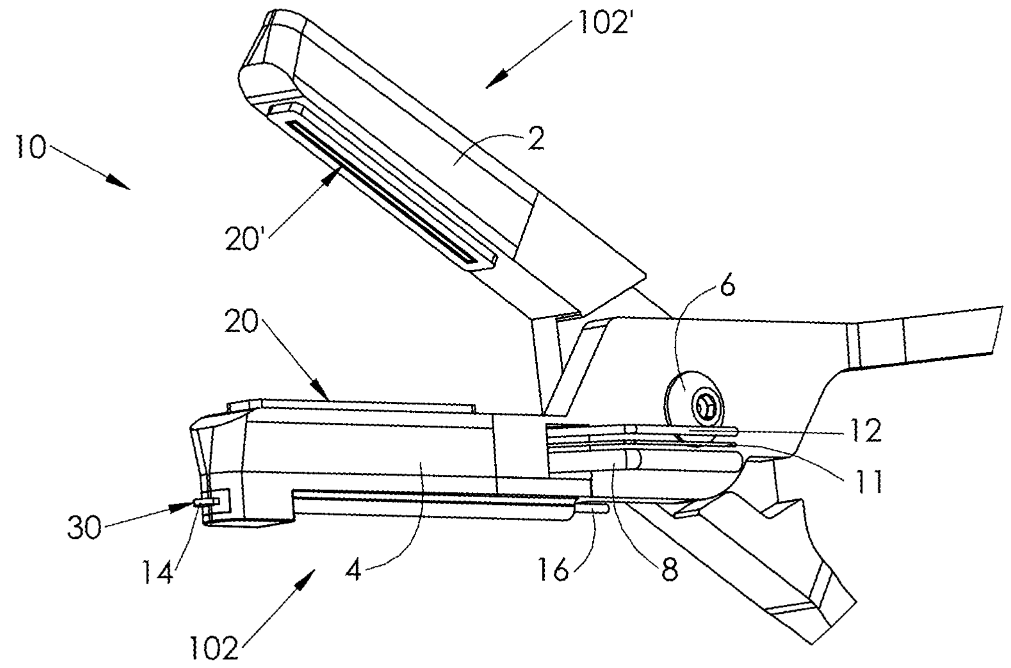
FIG. 1 shows a perspective view of one embodiment of the forceps assembly.
Figure 2:
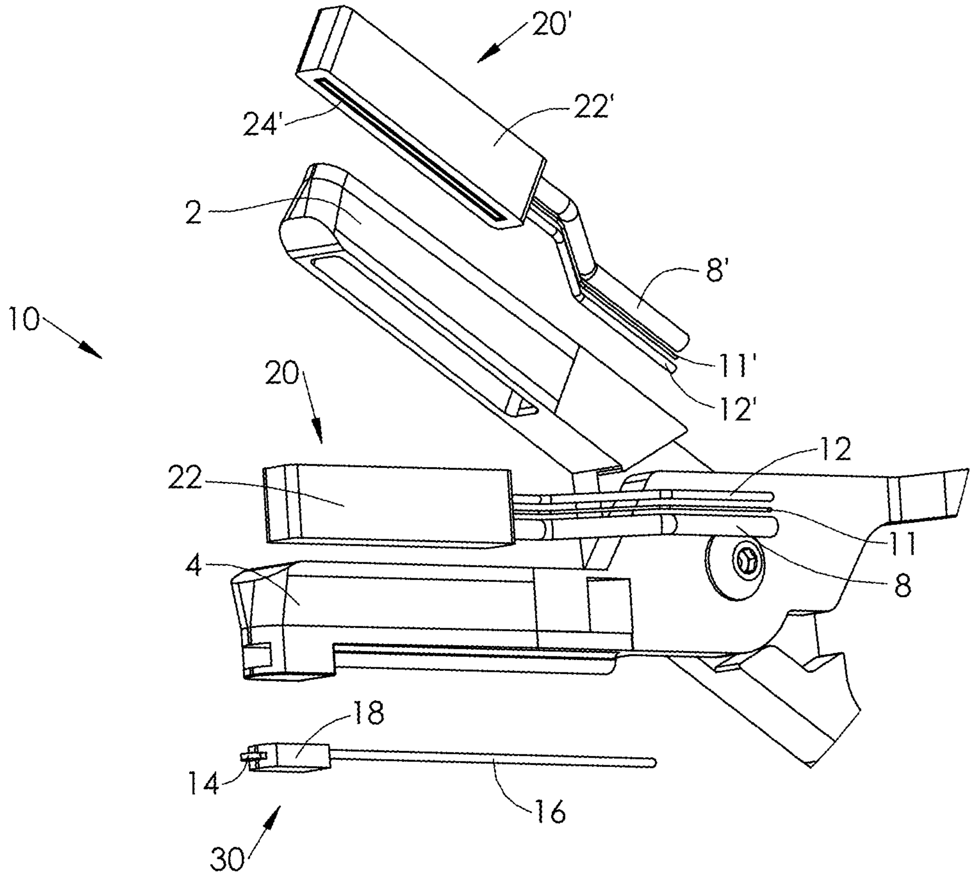
FIG. 2 shows an exploded view of one embodiment of forceps assembly.
Figure 3:
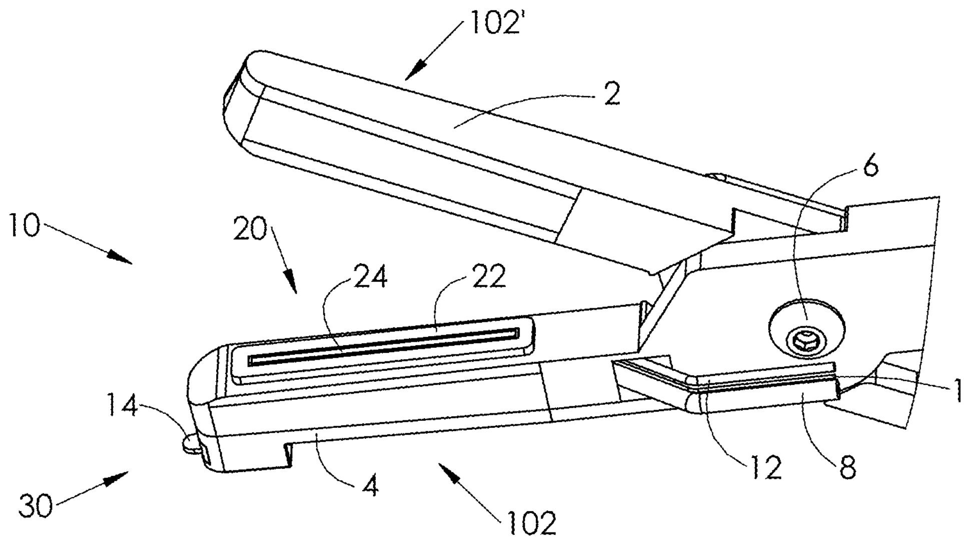
FIG. 3 shows a perspective view of one embodiment of the forceps assembly.
Figure 4:
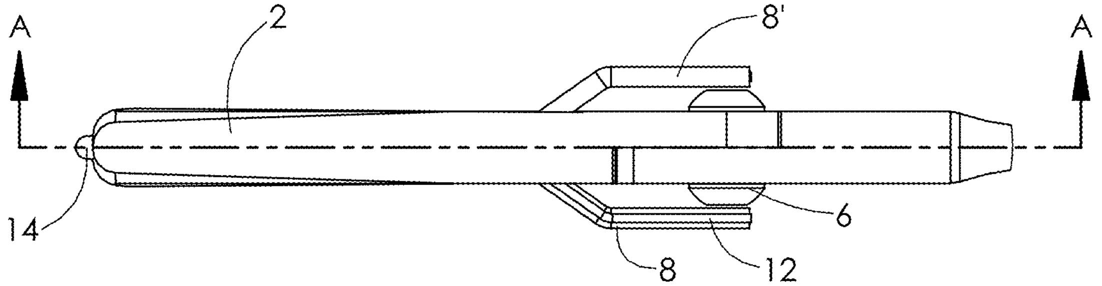
FIG. 4 shows a top view of forceps one embodiment of the assembly.
Figure 5:
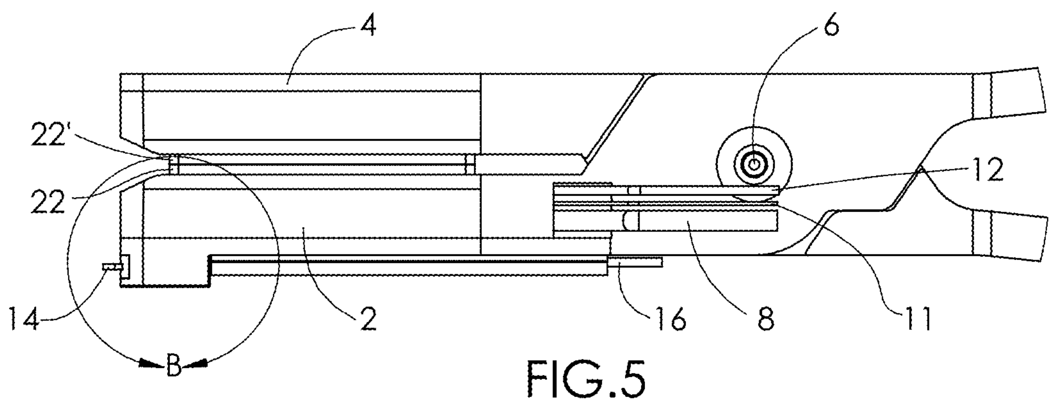
FIG. 5 shows a side elevation view of one embodiment of the forceps assembly.

In the associated figures together with the description herein, these and other features and advantages of exemplary embodiments of the present invention are set forth. Various embodiments of the present invention are described in detail with reference to the accompanying drawings. Wherever possible, the same or similar reference numerals are used in the drawings and the description to refer to the same or like parts or steps. In the following description, specific details are provided to provide an overall understanding of embodiments of the present invention and those skilled in the art will recognize that various changes and modifications of the embodiments described herein can be made without departing from the scope and spirit of the invention. Descriptions of well-known functions and constructions are omitted for the sake of clarity and conciseness.

In this specification "microwave" may be used broadly to indicate a frequency range of 300 MHz to 100 GHz, but preferably the range 1 GHz to 60 GHz. Specific frequencies that have been considered applicable (but not limited to) here are: 915 MHz, 2.45 GHz, 3.3 GHz, 5.8 GHz, 10 GHz, 14.5 GHz and 24 GHz. Furthermore, the specification use of "radio frequency" or "RF" indicates a frequency range extending up to 300 MHz. Frequency 10 kHz to 1 MHz will be used preferably for tissue cutting and are considered applicable (but not limited to) here.

As shown in the various views of FIGS. 1-5, the end effector assembly 10 typically comprises opposing jaws 102', 102 having a metal upper jaw body 2 and metal lower 4 jaw body, each preferably made from surgical grade stainless steel. Internally within a jaw body, a jaw has a heating and cutting insert assemblies 20', 20 having microwave heated absorbing parts 22', 20. Various embodiments and views of the components according to the present invention are also shown in the FIGS. 6-31.

Nested within the microwave absorbing parts 22, 22' of the heated inserts 20, 20' bodies are also separate secondary inserts 24, 24', through which RF energy is applied to to perform cutting, resection and/or dissection of the tissue retained between the jaws 102, 102' which is compressed by and between the jaws 102, 102', and functions separately from with the microwave energy applied to the microwave absorbing parts 22, 22'. A thin layer or coating (e.g. Teflon, PTFE) is needed to ensure a medical device does not accumulate any bacteria during procedures but also has high non-stick properties as well. The film thickness of most PTFE and resin bonded coatings applied to medical components is. 0003' shows. 0006' per surface, and may include an opening to permit inserts 24, 24' to make electrical contact with tissue for the desired procedure(s).

For blood vessel sealing, tissue heating, sealing and coagulation, the insert 20, 20' comprises respective microwave absorbing bodies 22 and 22' made from microwave absorbing (lossy) material, which is an direct contacts the treated tissue, and in another embodiment a thin layer of Teflon or silicone (not shown) between microwave absorbing material and treated tissue as an external protective layer.

The microwave absorbing parts 22, 22' of the jaws 102, 102' structures are preferably made from microwave absorbing material by means of extrusion, injection molding or machining. The microwave absorbing material can be silicone impregnated with silver (Ag) and glass fillers, which are generally unaffected by exposure to temperatures reaching 500° F. The glass fillers can be regular glass in form of small beads and other fillers include nickel (Ni), copper (Cu), Aluminum (Al), which can each be used as a single filler or combined with other materials, for example combinations of Ag/Cu; Ag/Al; Ag/Ni; Ag/Glass and others. Silicone is a preferred material due to compatibility to the human body, and other materials that can be used include fluorosilicone, fluorocarbon, monoplastic rubber and ethylene propylene diene monomer, and can be thermoplastic materials, such as rigid urethane impregnated with polyamide and thermoplastic urethane impregnated with carbonyl iron powder, iron silicide and ferrites fillers are utilized, and can be ceramic with different fillers, in view of advantageous microwave absorbing properties. When the microwave energy emitted by a microwave antenna, microwave absorbing material transforms the microwave energy into heat. The generated heat is applied to the treated tissue by means of capturing the tissue in the jaw structure and applying pressure on the tissue, depending on the used medical procedure, the sealing of the tissue or vessels, or welding and coagulation of the tissue. Microwave energy used here can be supplied by variety available on the medical market microwave generators, such as: "Solero" microwave generator by Angiodinamic operating with 2.45 GHz frequency or "Empring HP" ablation generator by Medtronic, or microwave generator for "Certus 140" by NeWave.

Figure 6:
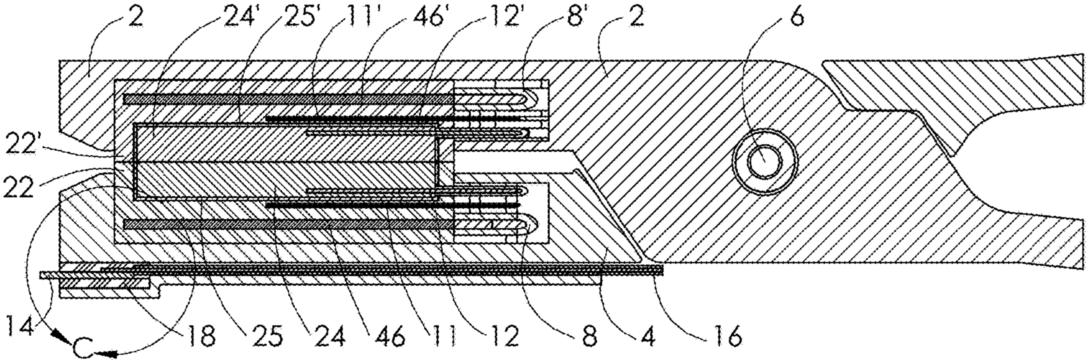
FIG. 6 shows section view of A-A taken from FIG. 4.
Figure 7:
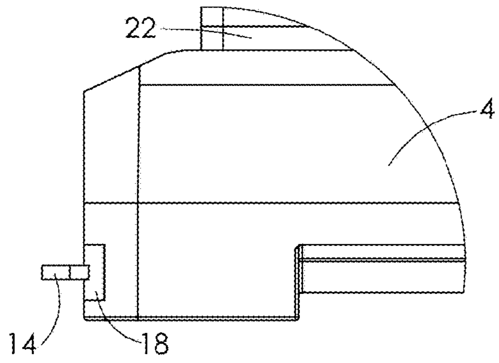
FIG. 7 shows an enlarged view B taken from FIG. 5.
Figure 8:
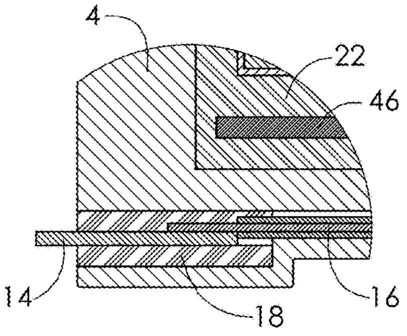
FIG. 8 shows an enlarged section view C taken from FIG. 6.
Figure 20:
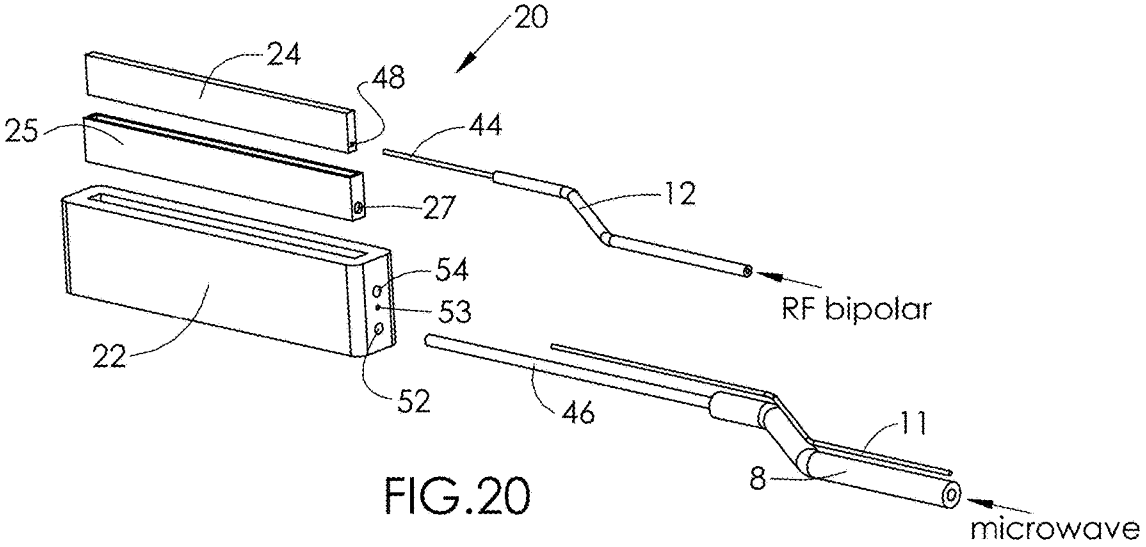
FIG. 20 shows an exploded view of heating and cutting insert one embodiment of the invention.
Figure 21:
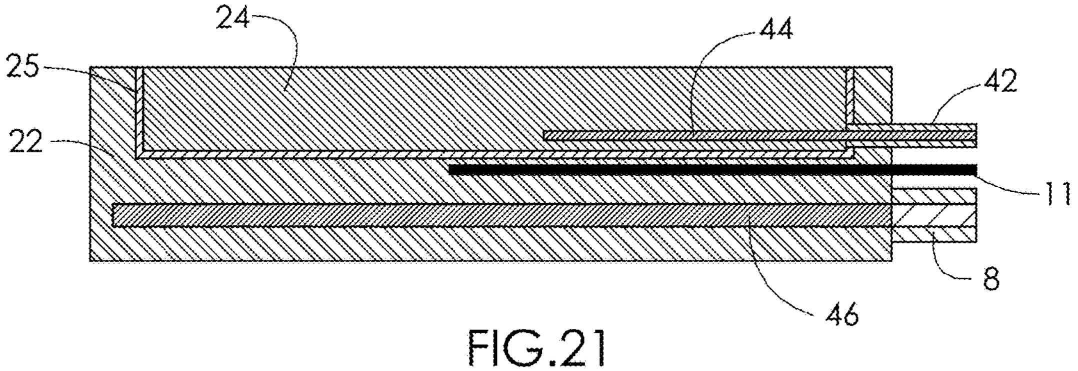
FIG. 21 shows section H-H taken from FIG. 19.
Figure 22:
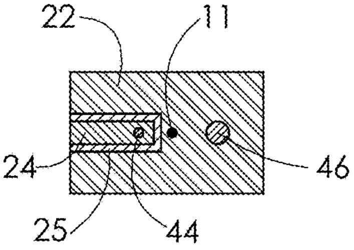
FIG. 22 shows a section G-G taken from FIG. 19.

As shown in FIGS. 6, 20, and 21, jaws 102, 102' structures each include a corresponding microwave antenna 46 and 46' for emitting energy in the microwave frequency range and located in a corresponding one of inserts bodies 22 and 22'. The microwave energy is supplied by coaxial cable 8 connected to the microwave energy generator (not shown). When microwave antenna delivers the microwave energy, the absorbing bodies 22 and 22' absorb the microwave energy. During the process of absorption of the microwave energy, the energy is transferred into heat. The generated heat is applied to the treated tissue by means of capturing the tissue in the jaw structure and applying pressure on the tissue, thus causing, depending on the medical procedure, the sealing of the tissue or vessels, or welding and coagulation of the tissue.

As described above, the heating and cutting insert assembly 20 also includes RF bipolar electrodes 24 and 24' for cutting the tissue compressed between jaws. Bipolar electrodes 24 and 24' are preferably located in the middle of the microwave absorbing bodies 22 and 22' width and at the surfaces of each microwave absorbing body facing and in contact with the tissue held within the jaws 102, 102'. Each of bipolar electrodes 24, 24' is connected, by bipolar RF cable 12, to the source of bipolar RF energy (not shown) suitable to perform the desired procedure. Bipolar electrodes 24 and 24' are each made from surgical grade stainless steel and the electrodes is shaped preferably as a thin strip with width from 0.010' to 0.020' typically having an edge extending toward the tissue (see FIGS. 18, 19). To avoid any effect from RF energy to microwave absorbing bodies 22 and 22', during cutting the tissue, bipolar electrodes 24 and 24' electrically insulated from the microwave absorbing bodies 22 and 22' by electrical insulation 25 and 25', but electrodes 24 and 24' contact area with tissue must not be electrically insulated.

Microwave absorbing bodies 22 and 22' can include temperature sensor(s) 11, 11' are connected to monitor and control (steps 135, 136, below) the temperature of microwave absorbing bodies and are received in apertures 53. The temperature sensors can be a thermocouple, a thermistor, or a fiber optic type and connect to cause the source of microwave energy to be adjusted to achieve the desired microwave absorbing body 22, 22' temperature.

In the bipolar electrosurgery, both the active electrode and return electrode functions are performed at the site of surgery and are located in the end effector jaws. Only the tissue grasped in the jaws is included in the electrical circuit for bipolar cutting of the tissue located between the jaws.

In the monopolar electrosurgery, the active electrode is placed at the surgical site. The patient return electrode (not shown, also known as a 'dispersive pad') is placed somewhere else on the patient's body. The current passes through the patient as it completes the circuit from the active electrode to the patient return electrode. The return electrode is not shown in the drawings for clarity. In the monopolar mode, an active electrode concentrates the current to the surgical site and a dispersive (return) electrode channels the current away from the patient.

The grounding pad should be placed close to the operative site on the ipsilateral side of the surgical field. Whenever feasible, the grounding pad should be positioned on well-vascularized areas of the body, preferably with substantial muscle mass. An example of one pad is the 3M® Universal Electrosurgical Pad 9160, and an example of positioning to provide a return path for the monopole circuit is shown in https://www.cehjournal.org/wp-content/uploads/Figure-2.png.

The tissue (not shown) in contact with monopolar electrode will be cut or dissected as desired. On today's medical market, there are available a wide variety of RF monopolar and bipolar energy generators that can be used with this apparatus, such as: "CELON PRECISION" by Olympus, "Bovie Specialist Pro" by Symmetry Surgical, "MultiGen2" by Stryker manufacturers.

Additionally, one of the jaws upper body 2 or lower body 4 can be equipped with an external monopolar RF electrode assembly 30 for tissue cutting and dissecting, and in presented drawings the assembly 30 incorporated with lower jaw body 4. The patient return electrode is placed somewhere else on the patient's body (not shown). The monopolar electrode 14 is connected to the source of monopolar RF energy (not shown) by a cable 16 and to avoid any passage of monopolar RF energy thru the metal jaw, monopolar electrode 14 electrically insulated from the lower jaw body 4 by insulation 18. The monopolar electrode 14 is preferably made from surgical grade stainless steel, and the exposed tip of the electrode 14 can have different shapes such as rounded (as shown), pointed etc. The electrode 14 should not have any sharp edges to avoid accidental tissue damage.

Figure 9:
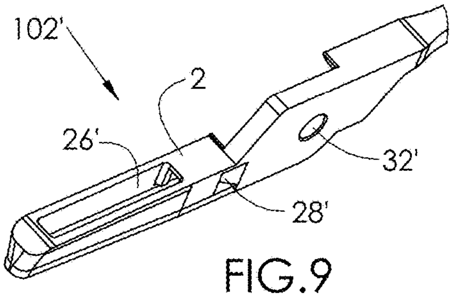
FIG. 9 shows a perspective view of forceps upper jaw.
Figure 10:
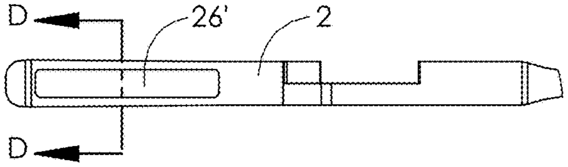
FIG. 10 shows a top view of forceps upper jaw.
Figure 11:
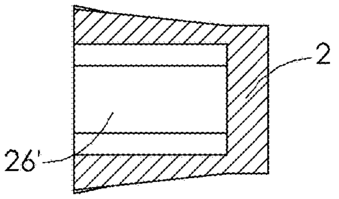
FIG. 11 shows section D-D taken from FIG. 10.
Figure 12:
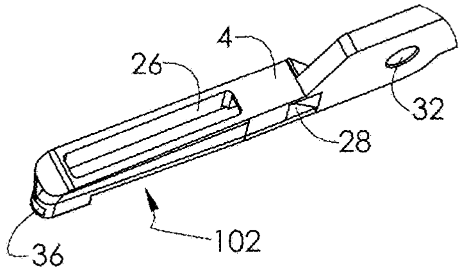
FIG. 12 shows a perspective view of forceps lower jaw.
Figure 13:
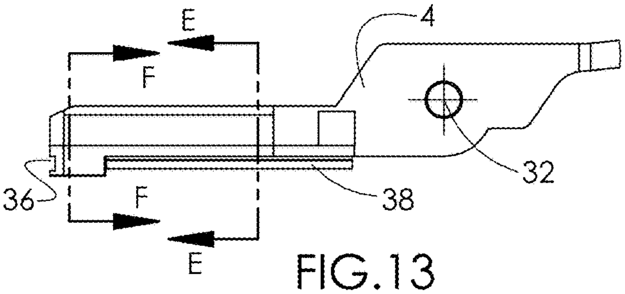
FIG. 13 shows a side elevation view of forceps lower jaw.
Figure 14:
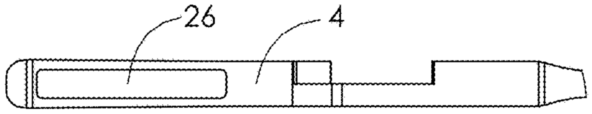
FIG. 14 shows a top view of forceps lower jaw.
Figure 15:
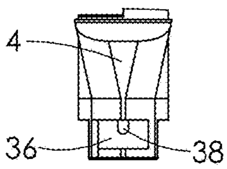
FIG. 15 shows a front elevation view of forceps lower jaw.
Figure 16:
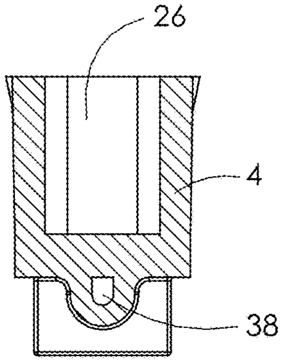
FIG. 16 shows a section (E-E of FIG. 13) of the lower jaw.
Figure 17:
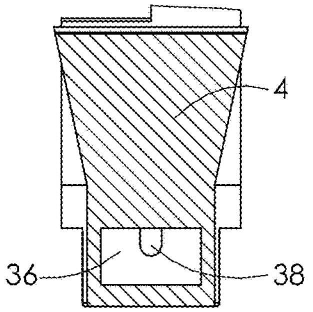
FIG. 17 shows a second section (F-F of FIG. 13) of the lower jaw.
Figure 18:
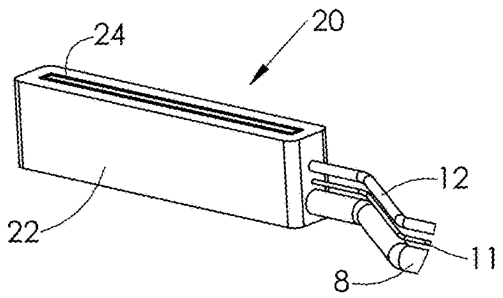
FIG. 18 shows a perspective view of one embodiment of the heating and cutting insert.
Figure 19:
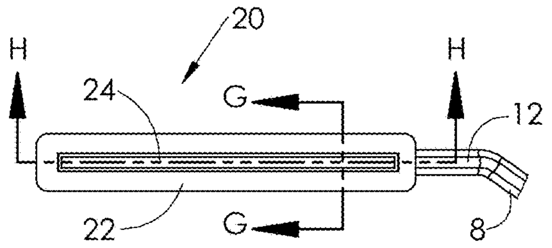
FIG. 19 shows a top view of heating and cutting insert of one embodiment of the invention.

As it shown in different views of end effector assembly 10, in FIG. 1 to FIG. 5, jaws 102 and 102' are assembled with heating and cutting insert assembly 20', 20 and lower jaw body 4 has a monopolar RF electrode assembly 30. Jaws 102 and 102' are pivotable each other about a pivotable hinge 6. Coaxial cables 8 and 8' are connected to supply microwave energy to microwave antennas 46 and 46' located, as it shown on sectional view in FIG. 6, as placed inside a microwave absorbing bodies 22 and 22'. Cables 12 and 12' supply bipolar RF energy to bipolar electrodes 24 and 24' and are located, as it shown on sectional view in FIG. 6, inside a microwave absorbing bodies 22 and 22', and electrodes 24 and 24' are electrically insulated from the microwave absorbing bodies 22 and 22' by electrical insulation 25 and 25'. The cable 16 supplies monopolar RF energy to the monopolar electrode 14 and is located in distal end of jaw 4 and forward of the distal end of the jaw 4 (away from the hinge 6) to electrically engage tissue intended to be cut by energy transmitted by the extending portion of the electrode 14, as shown in more details in exploded views FIG. 7 and FIG. 8, where electrical insulation 18 isolates electrode 14 from the metal jaw 4 body (the return electrode not shown). In FIG. 9 to FIG. 11 shown for better understandings, different views and section of upper jaw 102' showing preferable locations of the opening for heating and cutting inserts 26' and the opening 28' for microwave and RF cables 11, 12, and also showing the location of the jaw 102' pivotal hole 32'

In FIG. 12 to FIG. 17, shows different views and sections of lover jaw 102 where it shows, the preferable location of the opening 26 for heating and cutting inserts 20, and the opening 28 for microwave and RF cables (8, 11, 12), and the location of the jaw 102 pivotal hole 32. As it is shown, in sectional views (E-E and F-F of FIG. 13) in FIG. 16 and FIG. 17, the opening for monopolar electrode assembly 36 is located in the distal tip of the jaw 102' and structure for the RF cable for monopolar electrode 38 preferably located in the bottom of the jaw 102.

FIG. 18 through FIG. 22 show different views and sections of the heating 22 and cutting 24 insert assembly 20. The microwave absorbing body 22, made from microwave absorbing material, is shown having an opening 52 for microwave antenna 46. The coaxial cable 8 delivers microwave energy to microwave antenna 46 and when the microwave energy emitted by microwave antenna 8 microwave absorbing material is transferred the microwave energy into heat. The microwave absorbing body 22 has an opening 62 for bipolar electrode 24 and electrical insulation 25. The electrical insulation 25 provides electrical separation of the microwave absorbing body 22 and electrode 24 and electrode 24 have an opening 48 or place for electrical contact with RF energy cable 12 by a cable contact 44. The electrical connection can be done by welding or soldering. Insulation 25 includes an opening 27 for the passage of cable 12, and the microwave absorbing body has an opening for the cable 12. When RF energy delivered to electrodes 24 and 24', the tissue grasped between the jaws is included in the electrical circuit and performs a bipolar cutting of the tissue located between the jaws.

Figure 23:
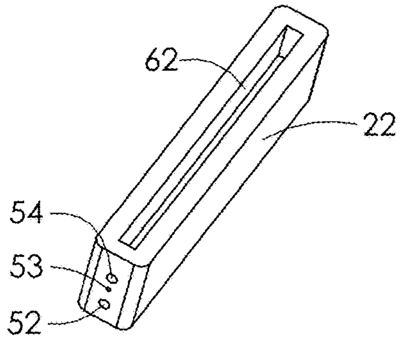
FIG. 23 shows a perspective view of microwave absorbing (lossy) material insert.

FIG. 23 shows a perspective view of microwave absorbing body 22 with an opening 62 for electrically insulated electrode 24 and with opening for microwave antenna 52 and opening for RF cable 54.

Figure 24:
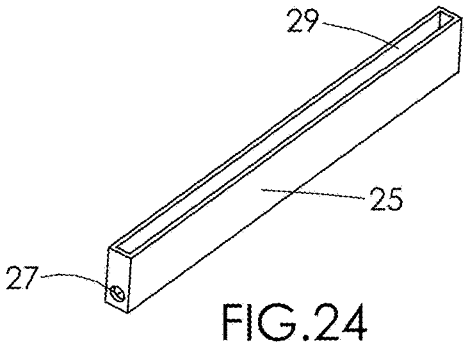
FIG. 24 shows a perspective view of bipolar electrode electrical insulation.
Figure 25:
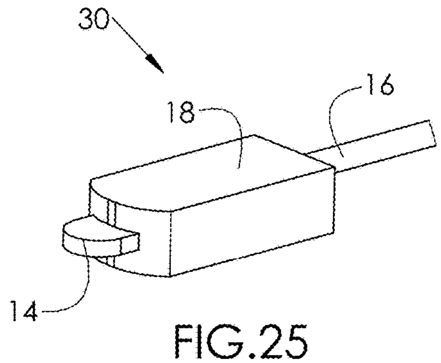
FIG. 25 shows a perspective view of monopolar electrode assembly one embodiment of the invention.
Figure 26:
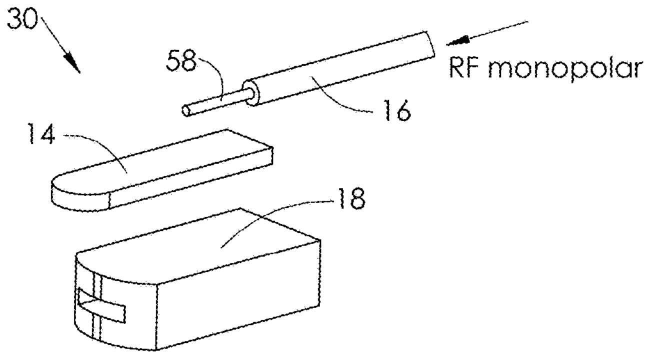
FIG. 26 shows an exploded view of monopolar electrode assembly of FIG. 25.
Figure 27:
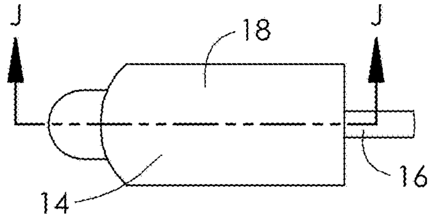
FIG. 27 shows a top of monopolar electrode assembly of FIG. 25.
Figure 28:
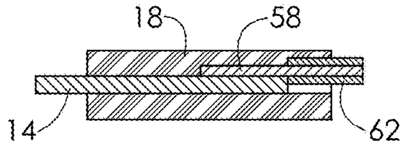
FIG. 28 shows section J-J taken from FIG. 27.

FIG. 24 is a perspective view of electrical insulation 25 with opening 29 for RF electrode 24 and opening for RF cable 27.

FIG. 25 to FIG. 28 shows different views of the monopolar electrode assembly 30. The monopolar electrode 14 is connected to RF energy cable 16 by electrical contact 58 e.g. by welding or soldering. The electrical insulation 18 electrically separates electrode 14 contact 58 from metal jaw body 4. When monopolar RF energy is applied to by cable 16 to electrode 14, the tissue in contact with monopolar electrode will be cut or dissected.

Figure 29:
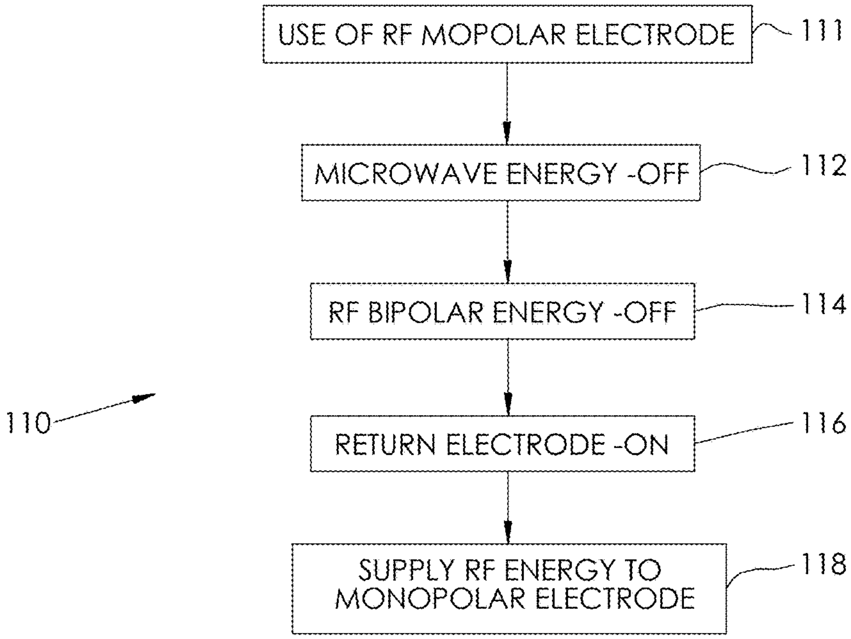
FIG. 29 shows a technological process flow chart when monopolar electrode is used according to one embodiment of the invention.
Figure 30:
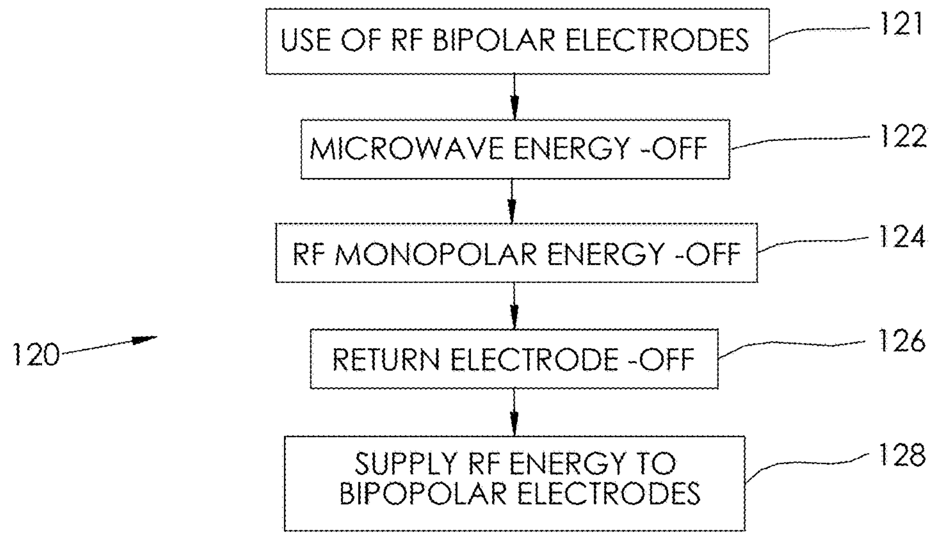
FIG. 30 shows a technological process flow chart when bipolar electrodes are used according to one embodiment of the invention.
Figure 31:
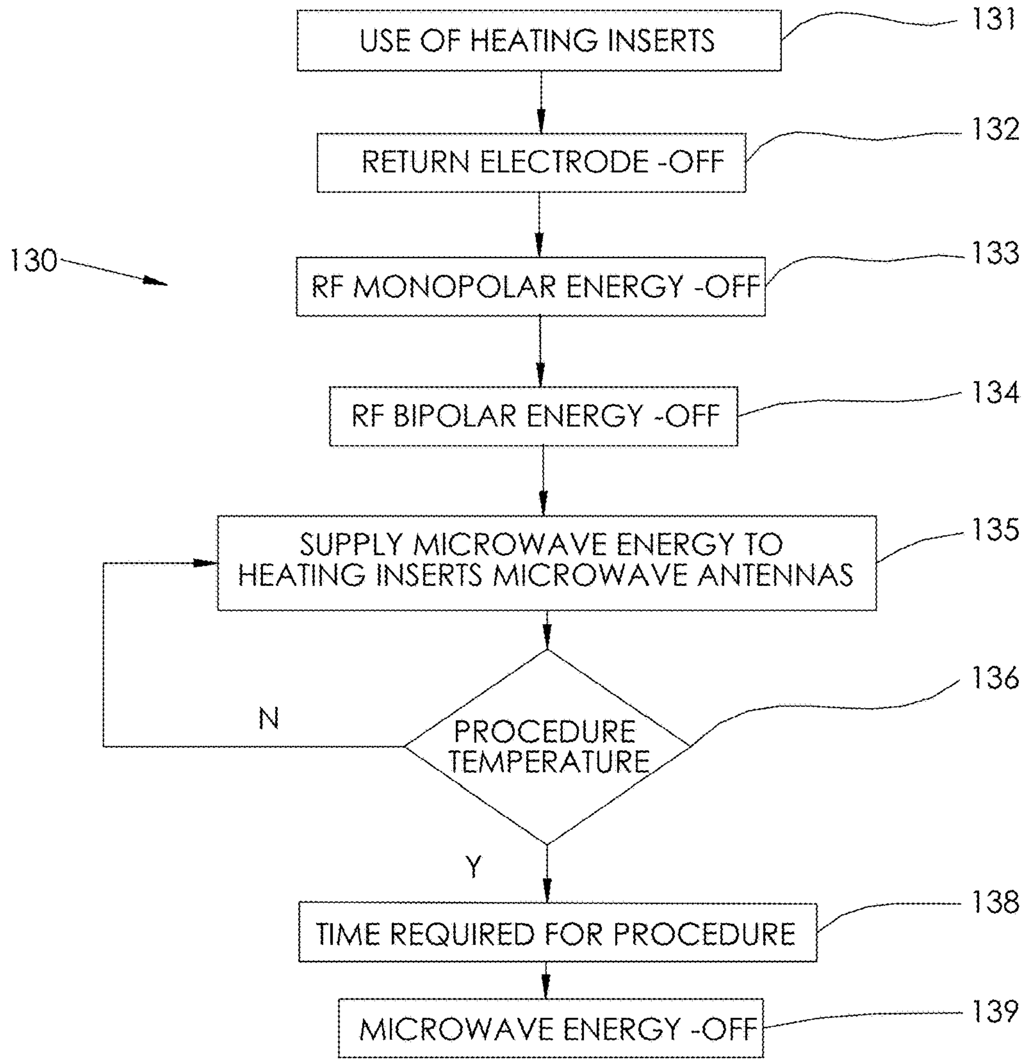
FIG. 31 shows a technological process flow chart when microwave antennas are used according to one embodiment of the invention.

Protocols for using the embodiments of the present invention are shown in FIGS. 29, 30, and 31, wherein FIG. 29 shows a technological flow chart 110 when monopolar electrode 14 is used 111 for cutting, dissecting, etc. Preferably, the microwave energy to antennae 24, 24' is turned off 112, and the bipolar (RF) energy feed to elements is also turned off 114. Confirmation that the return electrode (not shown) located at a different part of the body is connected and turned on 116 to provide a return path for the (RF) energy applied to the monopole electrode 14 is positioned in the body to contact the desired tissue, and the energy for cutting, dissection, etc. is supplied 118 to the monopole electrode 14 for a desired length of time.

The cutting (or other treatment) protocol of tissue between bipolar electrodes (22, 22') according to an embodiment of the present of FIG. 30 which shows a technological flow chart 120 which may be followed when bipolar electrodes (22, 22') are used, 121. Preferably, the microwave energy to antennae (24, 24') is turned off 122, and the monopolar (RF) energy feed to element 14 is also turned off 124, and the return electrode (not shown) is disconnected or removed, 126. The cutting (RF) energy is turned on and applied 128 by the electrode 14 to perform the desired action to tissue which contacts the antenna element 14.

A protocol for tissue is provided by FIG. 31 that shows a technological flow chart 130 when microwave antennas are used to transfer tissue heating energy into (microwave) energy absorbent materials (24', 24) in respective jaws (2, 4), 131, the return electrode (not shown) located at a different part of the body is turned off and/or disconnected, 132, and the monopolar (RF) energy is turned off, 133, as is the bipolar (RF) energy feed to elements is also turned off 134. Preferably, the microwave energy to antennae (46, 46') is applied 135 to perform the desired heating action to tissue between the jaws (2, 4) and in contact with heated materials (24, 24'). When temperature sensors (11, 11') are used, the temperature signal is monitored 136, and provides a signal to adjust (if not at the desired temperature) the supply energy sent to the antennae (46, 46') to maintain the desired temperature or effect. Once the temperature is stabilized, a time duration control 138 may also be applied, and the energy is removed 139 at the end of the procedure period.

These and further embodiments according to the invention as described shall not be limited except by the claims which follow.

What is claimed is:

1. A method of treating tissue, comprising:

selecting one of monopole cutting, bipolar cutting, and bipolar heating;

disabling a flow of energy for the monopole cutting, the bipolar cutting, and the bipolar heating if unselected;

applying a treatment apparatus corresponding to the selected one of monopole cutting, bipolar cutting, and bipolar heating;

applying energy corresponding to the selected one of monopole cutting, bipolar cutting, and bipolar heating to said treatment apparatus;

providing a pair of a facing first and a second metal jaw members movable between open and closed positions and having corresponding first and second facing surfaces capable of receiving tissue therebetween and;

coupling a microwave energy source to a microwave energy emitter contained within each of said paired facing jaw members;

wherein said bipolar heating comprises:

emitting microwave energy from each microwave energy emitter;

receiving said emitted microwave energy and providing heat from a microwave absorbing insert, made from microwave absorbing materials disposed in each of corresponding paired facing jaw members, each microwave absorbing insert being at least partially disposed between said corresponding microwave energy emitter and a corresponding one of said first and second facing surfaces of said paired jaw members and;

transferring heat energy from said microwave absorbing inserts to said corresponding facing surface of said first and second paired jaw members; and further providing RF energy from a bipolar radiofrequency (RF) energy source to a pair of electrodes wherein each electrode of said pair of electrodes is partially surrounded by a corresponding one of said microwave absorbing inserts, and each of said pair of electrodes is capable of contact with tissue received between said paired first and second metal jaw members.

2. The method of claim 1, wherein monopole cutting is selected and a locus of treatment is selected, the method further including connecting a return dispersive pad electrode apart from the locus of treatment.

3. The method of claim 2, wherein when bipolar cutting is selected, the step of applying energy comprises applying RF energy to the bipolar electrodes.

4. The method of claim 2, wherein when bipolar heating is selected, the step of applying energy comprises applying microwave energy to a bipolar antenna within each microwave absorbing insert.

5. The method of claim 4, further including monitoring the microwave absorbing insert temperature and providing a corresponding temperature signal.

6. The method of claim 5, wherein the applied microwave energy is controlled in response to the temperature signal.

7. The method of claim 1, wherein when monopole cutting is selected, the step of applying energy comprises applying RF energy to a monopole electrode extending outward from a metal jaw structure and electrically insulated therefrom, to be capable of cutting said tissue by RF energy from said monopole electrode.

* * * * *